(12) United States Patent
Mertz et al.

(10) Patent No.: US 7,881,765 B2
(45) Date of Patent: Feb. 1, 2011

(54) INTERFERENCE-FIT SHROUD-BASED CARDIAC ELECTRODES

(75) Inventors: John C. Mertz, Maple Grove, MN (US); Bryan J. Zart, Shakopee, MN (US); James Strom, Arden Hills, MN (US); Michael D. Fletcher, Minneapolis, MN (US); John E. Nicholson, Blaine, MN (US); Steven J. Fischer, Star Prairie, WI (US)

(73) Assignee: Medtronic, Inc., Minneapolis, MN (US)

( * ) Notice: Subject to any disclaimer, the term of this patent is extended or adjusted under 35 U.S.C. 154(b) by 908 days.

(21) Appl. No.: 11/380,773

(22) Filed: Apr. 28, 2006

(65) Prior Publication Data
US 2007/0255156 A1 Nov. 1, 2007

(51) Int. Cl.
*A61B 5/04* (2006.01)
(52) U.S. Cl. .................... 600/377; 607/36; 607/119
(58) Field of Classification Search ............. 600/372, 600/373, 374, 377; 607/9, 36, 116, 119
See application file for complete search history.

(56) References Cited

U.S. PATENT DOCUMENTS

| | | | |
|---|---|---|---|
| 3,983,867 A | 10/1976 | Case | |
| 4,023,565 A | 5/1977 | Ohlsson | |
| 4,082,086 A | 4/1978 | Page et al. | |
| 4,121,576 A | 10/1978 | Greensite | |
| 4,170,227 A | 10/1979 | Feldman et al. | |
| 4,186,947 A * | 2/1980 | Nixon | 285/112 |
| 4,263,919 A | 4/1981 | Levin | |
| 4,310,000 A | 1/1982 | Lindemans | |
| 4,313,443 A | 2/1982 | Lund | |
| 4,354,497 A * | 10/1982 | Kahn | 607/5 |
| 4,506,680 A | 3/1985 | Stokes | |
| 4,593,702 A | 6/1986 | Kepski et al. | |
| 5,331,966 A | 7/1994 | Bennett | |
| 5,431,695 A * | 7/1995 | Wiklund et al. | 607/36 |
| 5,776,188 A * | 7/1998 | Shepherd et al. | 623/2.38 |
| 6,205,358 B1 | 3/2001 | Haeg et al. | |
| 6,512,940 B1 * | 1/2003 | Brabec et al. | 600/374 |
| 6,522,915 B1 * | 2/2003 | Ceballos et al. | 600/509 |
| 6,768,128 B2 | 7/2004 | Kitamura et al. | |
| 6,997,949 B2 | 2/2006 | Tuch | |
| 2002/0147488 A1 * | 10/2002 | Doan et al. | 607/122 |
| 2004/0122481 A1 * | 6/2004 | Tidemand et al. | 607/37 |

* cited by examiner

*Primary Examiner*—Mark W Bockelman
*Assistant Examiner*—Roland Dinga
(74) *Attorney, Agent, or Firm*—Stephen W. Bauer; Reed A. Duthler

(57) ABSTRACT

Apparatus and method according to the disclosure relate to minimizing gaps between a substantially planar cardiac-sensing electrode and a shroud member utilizing a so-called interference-fit. For example, a relatively recessed area or aperture formed in an exemplary resin-based shroud member has slightly reduced dimensions relative to the electrode and requires compression forces during assembly (e.g., manually or in an automated process including a press, a tool or other means). The interference-fit promotes a very tight fit (or seal) between the metallic electrode and the resin-based shroud member and, importantly, minimizes gaps. Additionally, discrete interference structures promote fluid tight seals between the electrode and a recess or aperture adapted to receive the electrode.

18 Claims, 6 Drawing Sheets

INTERFERENCE-FIT SHROUD-BASED CARDIAC ELECTRODES

CROSS REFERENCE TO RELATED APPLICATION

The present patent document is related to co-pending non-provisional patent application Ser. No. 11/085,843, entitled, "APPARATUS AND METHODS OF MONITORING CARDIAC ACTIVITY UTILIZING IMPLANTABLE SHROUD-BASED ELECTRODES," filed on 22 Mar. 2005 the contents of which are hereby incorporated by reference.

FIELD OF THE INVENTION

The present invention relates generally to implantable medical devices and more particularly to a subcutaneous multiple electrode sensing and recording system for acquiring electrocardiographic data and waveform tracings from an implanted medical device without the need for or use of surface (skin) electrodes. More particularly, the present invention relates to implantable devices that are equipped with a shroud member that includes at least one electrode operatively coupled to sense cardiac activity wherein the electrode is mechanically coupled to the shroud member with minimal gaps or spaces therebetween. Minimizing the gaps or spaces tends to reduce risk of infection from body fluid that penetrates such a gap or space and thereafter chronically dwell in a relatively stagnant location.

BACKGROUND OF THE INVENTION

The electrocardiogram (ECG) is commonly used in medicine to determine the status of the electrical conduction system of the human heart. As practiced the ECG recording device is commonly attached to the patient via ECG leads connected to pads arrayed on the patient's body so as to achieve a recording that displays the cardiac waveforms in any one of 12 possible vectors.

Since the implantation of the first cardiac pacemaker, implantable medical device technology has advanced with the development of sophisticated, programmable cardiac pacemakers, pacemaker-cardioverter-defibrillator arrhythmia control devices and drug administration devices designed to detect arrhythmias and apply appropriate therapies. The detection and discrimination between various arrhythmic episodes in order to trigger the delivery of an appropriate therapy is of considerable interest. Prescription for implantation and programming of the implanted device are based on the analysis of the PQRST electrocardiogram (ECG) that currently requires externally attached electrodes and the electrogram (EGM) that requires implanted pacing leads. The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices are well known in the art. For example, S-T segment changes can be used to detect an ischemic episode. Acquisition and use of ECG tracing(s), on the other hand, has generally been limited to the use of an external ECG recording machine attached to the patient via surface electrodes of one sort or another.

The aforementioned ECG systems that utilize detection and analysis of the PQRST complex are all dependent upon the spatial orientation and number of electrodes available in or around the heart to pick up the depolarization wave front As the functional sophistication and complexity of implantable medical device systems increased over the years, it has become increasingly more important for such systems to include a system for facilitating communication between one implanted device and another implanted device and/or an external device, for example, a programming console, monitoring system, or the like. For diagnostic purposes, it is desirable that the implanted device be able to communicate information regarding the device's operational status and the patient's condition to the physician or clinician. State of the art implantable devices are available which can even transmit a digitized electrical signal to display electrical cardiac activity (e.g., an ECG, EGM, or the like) for storage and/or analysis by an external device. The surface ECG, in fact, has remained the standard diagnostic tool since the very beginning of pacing and remains so today.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. Of these, the twelve-lead electrocardiogram (ECG) is generally the first procedure used to determine cardiac status prior to implanting a pacing system; thereafter, the physician will normally use an ECG available through the programmer to check the pacemaker's efficacy after implantation. Such ECG tracings are placed into the patient's records and used for comparison to more recent tracings. It must be noted, however, that whenever an ECG recording is required (whether through a direct connection to an ECG recording device or to a pacemaker programmer), external electrodes and leads must be used.

Unfortunately, surface electrodes have some serious drawbacks. For example, electrocardiogram analysis performed using existing external or body surface ECG systems can be limited by mechanical problems and poor signal quality. Electrodes attached externally to the body are a major source of signal quality problems and analysis errors because of susceptibility to interference such as muscle noise, power line interference, high frequency communication equipment interference, and baseline shift from respiration or motion. Signal degradation also occurs due to contact problems, ECG waveform artifacts, and patient discomfort. Externally attached electrodes are subject to motion artifacts from positional changes and the relative displacement between the skin and the electrodes. Furthermore, external electrodes require special skin preparation to ensure adequate electrical contact. Such preparation, along with positioning the electrode and attachment of the ECG lead to the electrode needlessly prolongs the pacemaker follow-up session. One possible approach is to equip the implanted pacemaker with the ability to detect cardiac signals and transform them into a tracing that is the same as or comparable to tracings obtainable via ECG leads attached to surface electrodes.

Previous art describes how to monitor electrical activity of the human heart for diagnostic and related medical purposes. U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems, which combine surface EKG signals for artifact rejection.

The primary use for multiple electrode systems in the prior art is vector cardiography from ECG signals taken from multiple chest and limb electrodes. This is a technique whereby the direction of depolarization of the heart is monitored, as well as the amplitude. U.S. Pat. No. 4,121,576 issued to Greensite discusses such a system.

Numerous body surface ECG monitoring electrode systems have been employed in the past in detecting the ECG and conducting vector cardiographic studies. For example, U.S. Pat. No. 4,082,086 to Page, et al., discloses a four electrode orthogonal array that may be applied to the patient's skin both for convenience and to ensure the precise orientation of one electrode to the other. U.S. Pat. No. 3,983,867 to Case describes a vector cardiography system employing ECG electrodes disposed on the patient in normal locations and a hex axial reference system orthogonal display for displaying ECG signals of voltage versus time generated across sampled bipolar electrode pairs.

With regard to various aspects of time-release of surface coatings and the like for chronically implanted medical devices, the following issued patents are incorporated herein by reference. U.S. Pat. Nos. 6,997,949 entitled, "Medical device for delivering a therapeutic agent and method of preparation," and 4,506,680 entitled, "Drug dispensing body implantable lead." Moreover, in regard to subcutaneously implanted EGM electrodes, the aforementioned Lindemans U.S. Pat. No. 4,310,000 discloses one or more reference sensing electrode positioned on the surface of the pacemaker case as described above. U.S. Pat. No. 4,313,443 issued to Lund describes a subcutaneously implanted electrode or electrodes for use in monitoring the ECG. Finally, U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes (located on the body of an implanted device).

SUMMARY OF THE INVENTION

The present invention provides a leadless subcutaneous (or submuscular) single or multiple-electrode array that provides various embodiments of a compliant surround shroud coupled to a peripheral portion of an implantable medical device (IMD). The shroud incorporates a plurality of substantially planar electrodes mechanically coupled within recessed portions of the shroud using specially adapted interference fittings.

These electrodes electrically couple to circuitry of an IMD and are adapted to detect cardiac activity of a subject. Temporal recordings of the detected cardiac activity are referred to herein as an extra-cardiac electrogram (EC-EGM). The recordings can be stored upon computer readable media within an IMD at various resolution (e.g., continuous beat-by-beat, periodic, triggered, mean value, average value, etc.). Real time or stored EC-EGM signals can be provided to remote equipment via telemetry. For example, when telemetry, or programming, head of an IMD programming apparatus is positioned within range of an IMD the programmer receives some or all of the EC-EGM signals.

The present invention relates generally to implantable medical devices and more particularly to a subcutaneous multiple electrode sensing and recording system for acquiring electrocardiographic data and waveform tracings from an implanted medical device without the need for or use of surface (skin) electrodes. More particularly, the present invention relates to implantable devices that are equipped with a shroud member that includes at least one electrode operatively coupled to sense cardiac activity wherein the electrode is mechanically coupled to the shroud member with minimal gaps or spaces therebetween. Minimizing the gaps or spaces tends to reduce risk of infection from body fluid that penetrates such a gap or space and thereafter chronically dwell in a relatively stagnant location.

One method to minimize gaps between the substantially planar electrodes and a shroud member utilizes a so-called interference-fit. For example, a relatively recessed area or aperture formed in an exemplary resin-based shroud member has slightly reduced dimensions relative to the electrode and requires compression forces during assembly (e.g., manually or in an automated process including a press, a tool or other means). The interference-fit promotes a very tight fit (or seal) between the metallic electrode and the resin-based shroud member and, importantly, minimizes gaps. It also provides frictional forces that tend to retain the parts in place.

Such an interference-fit can be enhanced with use of ribs, bosses, or other structures disposed on the electrode and/or the shroud member which increase interference in selected areas between the electrode and shroud member. Such structures tend to enhance the fit between the electrode and shroud member without significantly increasing insertion forces.

In the family of shroud-based electrodes according to the invention, some embodiments include mechanical gaps in the device that could be possible breeding spaces for infectious bacteria, following implant. Since infection is a potentially serious complication, the inventors addressed many ways to mitigate the threat.

The present invention provides improved apparatus and methods for reliably collecting EC-EGM signals for use or collection in conjunction with diverse IMDs (e.g., implantable pacemakers having endocardial leads, implantable cardioverter-defibrillators or ICDs, drug delivery pumps, subcutaneous ICDs, submuscular ICDs, brain stimulation devices, nerve stimulation devices, muscle stimulation devices and the like).

The invention can be implemented employing suitable sensing amplifiers, switching circuits, signal processors, and memory to process the EC-EGM signals collected between any selected pair or pairs of the electrodes deployed in an array around the periphery of an IMD to provide a leadless, orientation-insensitive means for receiving the EC-EGM signals from the heart.

The shroud can comprise a non-conductive, bio-compatible material such as any appropriate resin-based material, urethane polymer, silicone, or relatively soft urethane that retains its mechanical integrity during manufacturing and prolonged exposure to body fluids. The shroud placed around the peripheral portions of an IMD can utilize a number of configurations (e.g., two, three, four recesses) for individual electrodes. However, a four-electrode embodiment appears to provide an improved signal-to-noise ratio than the three-electrode embodiment. And, embodiments having a single electrode pair appear much more sensitive to appropriate orientation of the device relative to the heart than embodiments having more than a single pair of electrodes. Of course, embodiments of the invention using more than four electrodes increase complexity without providing a significant improvement in signal quality.

Embodiments having electrodes connected to three sense-amplifiers that are hardwired to three electrodes can record simultaneous EC-EGM signals. Alternative embodiments employ electrodes on the face of the lead connector, or header module, and/or major planar face(s) of the pacemaker that may be selectively or sequentially coupled in one or more pairs to the terminals of one or more sense amplifiers to pick up, amplify and process the EC-EGM signals across each electrode pair. In one aspect, the EC-EGM signals from a first electrode pair are stored and compared to other electrode pair(s) in order to determine the optimal sensing vector. Following such an optimization procedure, the system can be programmed to chronically employ the selected subcutaneous EC-EGM signal vector.

The three electrode and three amplifier embodiment offers several advantages including ability to sense cardiac activity in virtually every direction by adjusting the selected sensing vector.

Prior art U.S. Pat. No. 5,331,966 had electrodes placed on the face of the implanted pacemaker. When facing muscle tissue, the electrodes were apt to detect myopotentials and were susceptible to baseline drift. The present invention minimizes myopotentials and allows the device to be implanted in a variety of subcutaneous or submuscular locations of a patient's thorax by providing maximum electrode separation and minimal signal variation due to various orientation of an IMD within a surgically-created pocket because the electrodes are placed on the surround shroud in such a way as to maximize the distance between electrode pairs. The shroud provides insulation from the typically metallic IMD casing due to the insulative properties of the compliant shroud and recesses where the electrodes are mechanically coupled. The electrode placement maintains a maximum and equal distance between the electrode pairs. Such spacing with the four-electrode embodiment maintains maximum average signal due to the fact that the spacing of the two vectors is equal and the angle between these vectors is 90°, as known in the art and as predicted via mathematical modeling. Such orthogonal spacing of the electrode pairs also minimizes signal variation. An alternate three-electrode embodiment provides the electrodes arranged within the surround shroud in an equilateral triangle along the perimeter of the implanted pacemaker. Vectors in this embodiment can be combined to provide adequate sensing of cardiac signals.

Certain embodiments of the invention utilize substantially planar electrodes having one or more time-release coatings on at least a portion of the exposed surfaces thereof, or all surfaces of the planar portions and the elongated conductor portion thereof. In the event that an increase in surface area of the electrodes is desired and/or a means of retaining more of the time-release coating(s), a layer of material can be used (e.g., titanium nitride, platinum black, or the like).

With respect to the elongated conductor coupling the planar electrodes to operative circuitry within an IMD, the assembly can comprise a unitary member stamped from a plate of conductive material such as titanium. In one embodiment the unitary member comprises a pre-shaped partially serpentine workpiece having a slightly curvilinear (i.e., substantially planar) major plate portion, a transition portion, and a partially serpentine portion adapted to cooperate with the configuration of the pre-configured conductor pathway.

For mass production of assemblies according to the invention a unique electrode piecepart can be fabricated for each unique conductor pathway and recess shape and configuration (including any of the variety of diverse mechanical interlocking features described hereinabove). Besides manufacturing processes such as metal stamping, the metallic electrode member(s) can be fabricating using electron discharge machining (EDM), laser cutting, or the like. It is desirable that the electrode assemblies are pre-configured (at least in a two-dimensional (2D) manner) so that little or no mechanical deformation or bending is required to fit each assembly into a shroud member. In addition, due to pre-configuring the parts the bends occur in a highly predictable manner and retain relatively little, if any, energy due to the spring-constant of the metal used to form the parts. In the event that electrical insulation or a dielectric layer becomes necessary or desirable, the major elongated portion of an electrode assembly can be coated with an insulative material such as paralyne or similar while the portions of the assembly likely to contact body fluid can be coating with diverse coatings pursuant to various embodiments of the invention.

In addition to a permanent surface coating for the electrodes such as titanium nitride for titanium electrode assemblies, and the diverse time-release materials of the invention, the surfaces of the electrodes may require temporary protection during manual handling to prevent contamination. A coating, such as may be provided by Dexamethazone Sodium Phosphate, NaCL (salts) and sugar solutions, provides such protection as well as enhancing the wetting of the electrode surface after implant. Conductive hydro gels, applied wet and allowed to dry, may also be applied to the electrode surfaces to protect them from damage during handling while helping to prevent contamination.

Electrode assemblies according to the invention can be used for chronic or acute EC-EGM signal sensing collection and attendant heart rate monitoring, capture detection, arrhythmia detection, and the like as well as detection of myriad other cardiac insults (e.g., ischemia monitoring using S-T segment changes, pulmonary edema monitoring based upon impedance changes).

Electrode assemblies according to the invention increase ease of fabrication due to the pre-formed parts and mechanical interlocking features and increase signal-to-noise ratio due to the relatively large surface area of the planar electrodes. In addition, manufacturing yield improvements are realized due to enhanced alignment of the proximal end portions of the pre-formed elongated conductors relative to multi-polar electrical feedthrough arrays. Yield improvements due to the unique length and shape of each discrete electrode part are also realized when practicing the invention. That is, a person assembling an IMD or during a pre-assembly inspection, according to certain aspects of the invention, can expect the feedthrough terminations and the terminations to be accurately inserted and aligned per a desired specification. The invention also offers advantages for automating all or a part of the fabrication process including laser welding the terminations together.

In addition, the surface of the electrode can be treated with one or more electrode coatings to enhance signal-conducting, de- and re-polarization sensing properties, and to reduce polarization voltages (e.g., platinum black, titanium nitride, titanium oxide, iridium oxide, carbon, etc.). That is the surface area of the electrode surfaces may be increased by techniques known in the art. For example, the surfaces may be roughened or texturized or otherwise made porous and/or microporous and/or can be coated with such materials as just described and equivalents thereof. All of these materials are known to increase the true electrical surface area to improve the efficiency of electrical performance by reducing wasteful electrode polarization, among other advantages.

The materials can be applied using any of a variety of techniques such as by sputtering, electron beam deposition, CVD or the like. Some coatings, such as steroid-eluting materials, can become more important over time as such enhancing coatings can help as the electrodes (typically) become encapsulated in scar tissue and thus at least indirectly contact with the body tissue. Such indirect tissue contact can damp the cardiac signals thus negatively affecting the sensing and detection ability of uncoated electrode(s).

Many of the embodiments of the inventive electrodes herein can provide a continuous electrical path free of welds or bonds on a portion of the planar electrode, the transition portion, the elongated conductor or the distal tip portion. Moreover, the electrode assembly according to the invention anchors to a shroud member free of any chemical or adhesive bonding materials that can cause excursions due to electroactive specie release to the electrode surface or portions thereof.

These and other advantageous aspects of the invention will be appreciated by those of skill in the art after studying the invention herein described, depicted and claimed. In addition, persons of skill in the art will appreciate insubstantial modifications of the invention that are intended to be expressly covered by the appended claims.

DETAILED DESCRIPTION OF THE DRAWINGS

Figure 1:
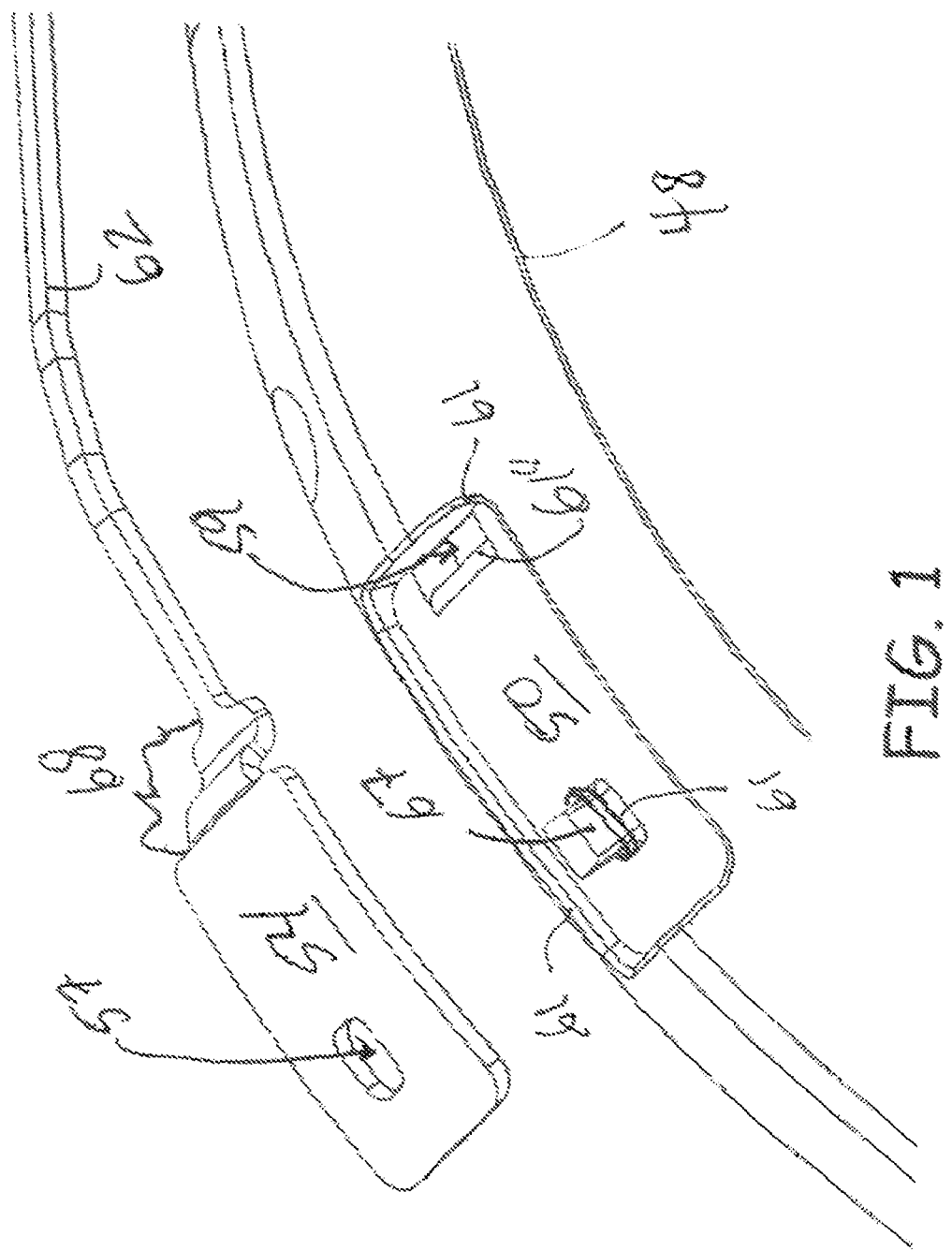
FIG. 1 is an exploded view depicting an exemplary electrode adjacent an electrode receiving recess according to one embodiment of the invention.

FIG. 1 is an exploded view depicting an exemplary electrode 54 adjacent an electrode receiving recess 50 according to one embodiment of the invention. Also depicted in FIG. 1 is an optional aperture 57 formed in the electrode 54 for receiving a connector 67 as well as the aperture 59 for receiving and, preferably, interlocking with the transitional portion 68 of the electrode 54. Used in combination the connector 67 and the aperture 57 and the transitional portion 68-aperture 59 provide two discrete fixation locations for the electrode 54. For example the aperture 59 can be located at any portion of the periphery or major part of the recess 50 to provide a discrete retaining force. In addition to or in lieu of the foregoing one or more connector members 67 can provide other discrete fixation locations for the electrode 54.

The connector 67 can comprise a unitary member adapted to receive an ultrasonic bonding horn to thus form a rivet-like enlarged head portion to increase the fixation of the electrode 54 and/or can comprise a split member which expands after the electrode 54 is fully mounted. Such a split member can include an enlarged head portion for retaining the electrode (with or absent ultrasonic bonding of same).

As known in the art of ultrasonic bonding an ultrasonic head couples to the connector 67 which can comprise a thermoplastic or resin-based material and the material quickly deforms; in this case, the material deforms to provide additional mechanical fixation to the substantially planar electrode 54. The operative head of the ultrasonic head can be configured to only impinge upon the connector 67 and not with any surrounding part of the shroud 48 (e.g., the edges of the recess 50, etc.). While not specifically depicted herein, in this aspect of the invention the head comprises an effective head portion adapted specifically for producing a weld nugget on the upper portion of connector 67. Issued U.S. Pat. No. 6,205,358 entitled "Method of Making Ultrasonically Welded, Staked or Swaged Components in an Implantable Medical Device" and assigned to Medtronic, Inc. describes and depicts some aspects of ultrasonic welding and the entire contents of the '358 patent are hereby incorporated herein. Also, U.S. Pat. No. 6,768,128 entitled "Ultrasonic-Welding Apparatus, Optical Sensor and Rotation Sensor for the Ultrasonic-Welding Apparatus is hereby incorporated herein by reference.

Figure 2:
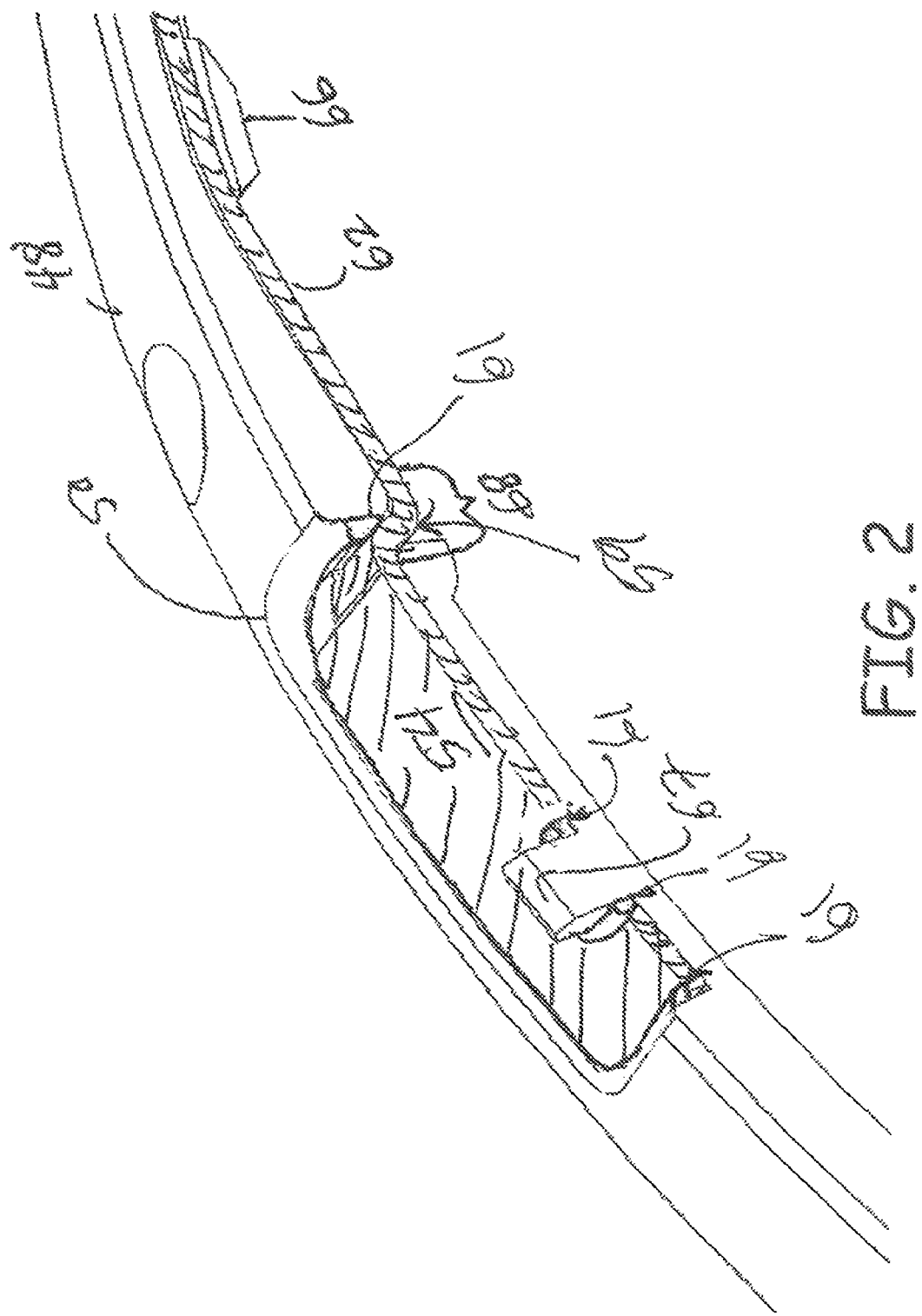
FIG. 2 depicts in perspective view a cross-sectional portion of an electrode-receiving recess having an electrode coupled therein according to one embodiment of the invention.

FIG. 2 depicts in perspective view a cross-sectional portion of an electrode-receiving recess 50 having an electrode 54 coupled therein according to one embodiment of the invention. In the depicted embodiment the connector 67 comprises an axially split member (with just one half illustrated) as just described. Similarly, only half of the member 66 is depicted due to the cross-sectional view employed. The transitional portion 68 of the electrode assembly is shown effectively interlocked with aperture 59. In the depicted embodiment opposing surfaces of the aperture 59 mechanically cooperate with surface portions of the transitional portion 68 to effectively provide three-dimensional (3D) mechanical support thereto.

Figure 3:
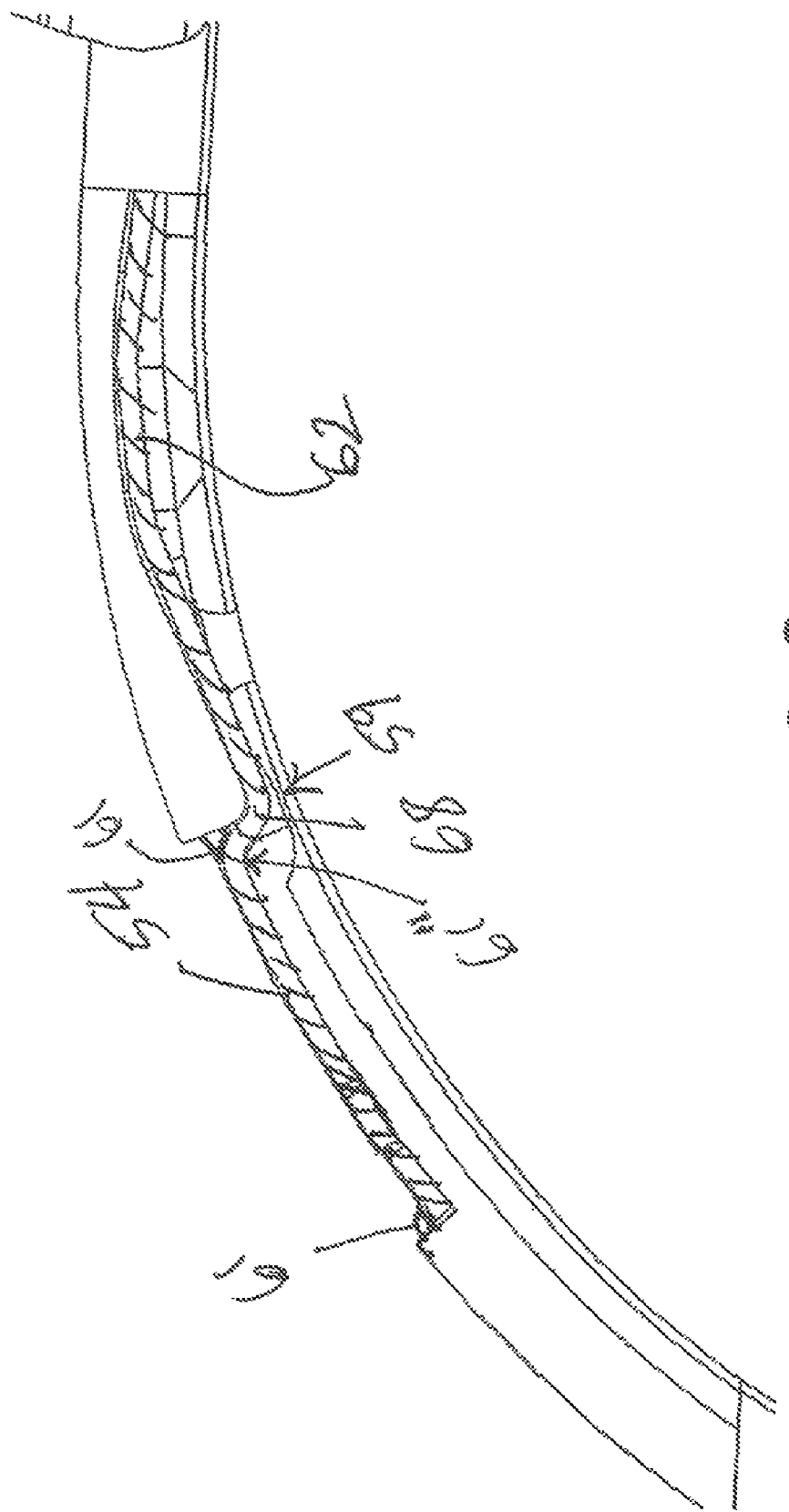
FIG. 3 is an elevational view in cross-section of the electrode-receiving recess having an electrode coupled therein according to an embodiment of the invention wherein the electrode is devoid of apertures and the corresponding recess is devoid of a central connector member.

Referring now to FIG. 3, an elevational view in cross-section of the electrode-receiving recess 50 having an electrode 54 coupled therein according to one embodiment of the invention is illustrated. In the embodiment depicted in FIG. 3 the electrode 54 is devoid of apertures (e.g., aperture 57 of FIG. 1) and the corresponding recess 50 is devoid of a central connector member (e.g., connector 57 of FIG. 1). In this view at a mechanical interference structure 61 is depicted around an upper major surface of the electrode 54.

Also depicted in FIG. 3 is an auxiliary interference structure (denoted by arrow 61"). Of course, other shapes and geometries than those illustrated for structure 61 and auxiliary structure 61" can be effectively utilized to promote sealing mechanical support. For example, auxiliary structure 61" can comprise one or more rib members disposed in or on select portions of the electrode 54 and/or the recess 50. Such rib members which increase the interference forces in selected abutting locations between electrode 54 and shroud 48. For example, as depicted in FIG. 3, a transverse rib 61" adjacent aperture 59 can be utilized to increase positive engagement between interference structure 61 and transitional portion 68 of an elongated conductor 62 coupling the electrode 54 to active circuitry. And, if a connector member 67 is used to retain the electrode 54 within the recess (or aperture) 50 the retention requirements (i.e., for a fluid tight seal) around the periphery of the electrode 54 can perhaps be relaxed.

Figure 4:
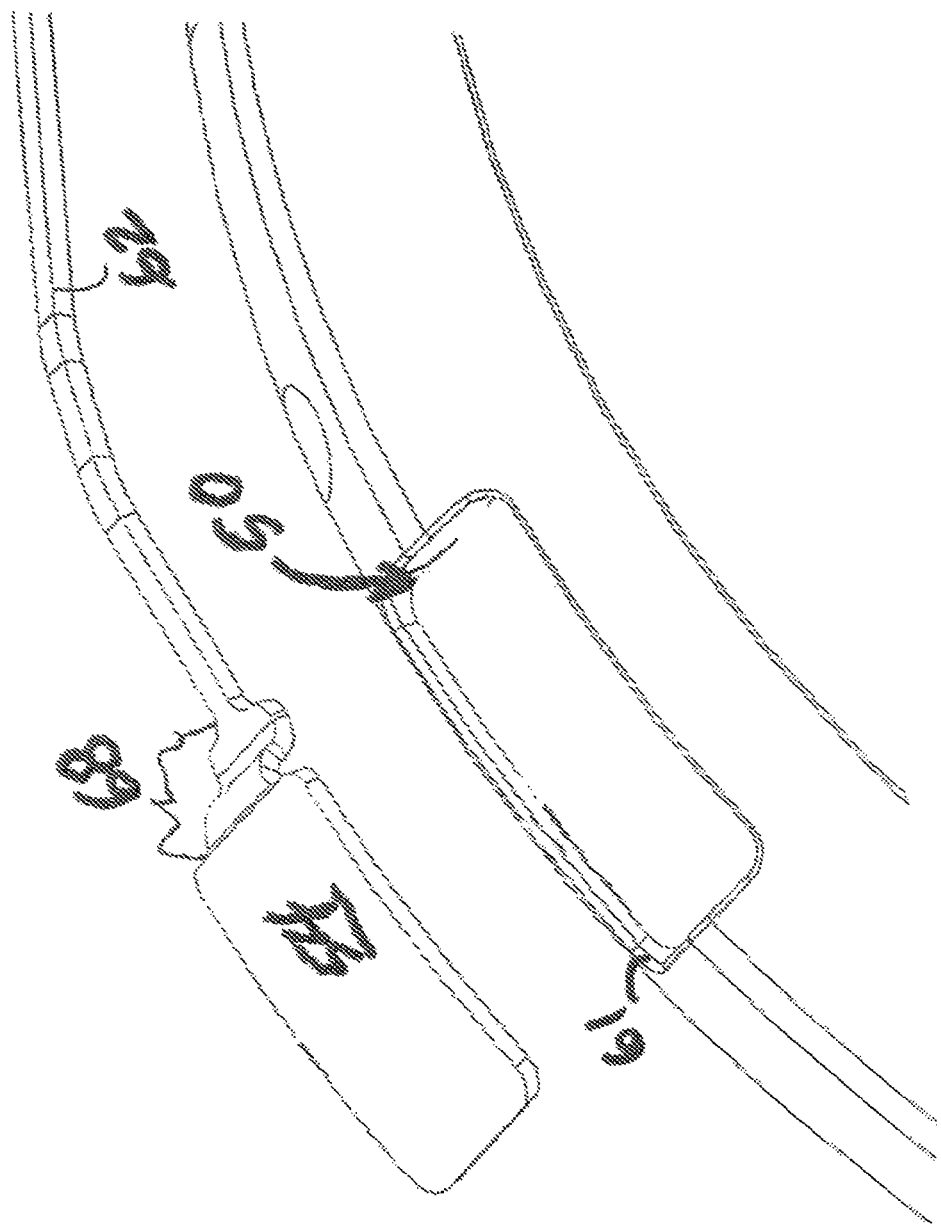
FIG. 4 is a perspective view of an exploded assembly according to an embodiment of the invention wherein the electrode is free of apertures and resides in an aperture formed in the shroud member surrounded by interference structures.

Referring now to FIG. 4, which is a perspective view of an exploded assembly according to an embodiment of the invention wherein the electrode 54 is free of apertures (e.g., aperture 57 of FIG. 1) and resides in an aperture 50 formed in the shroud member 48 (in lieu of recess 50 of FIG. 1). The aperture 50 is surrounded by interference structures 61 which can comprise a protruding lip, shelf-like feature, geometric, regular or irregular feature designed to deflect slightly when the electrode 54 is compressed into position in the aperture 50.

Figure 5:
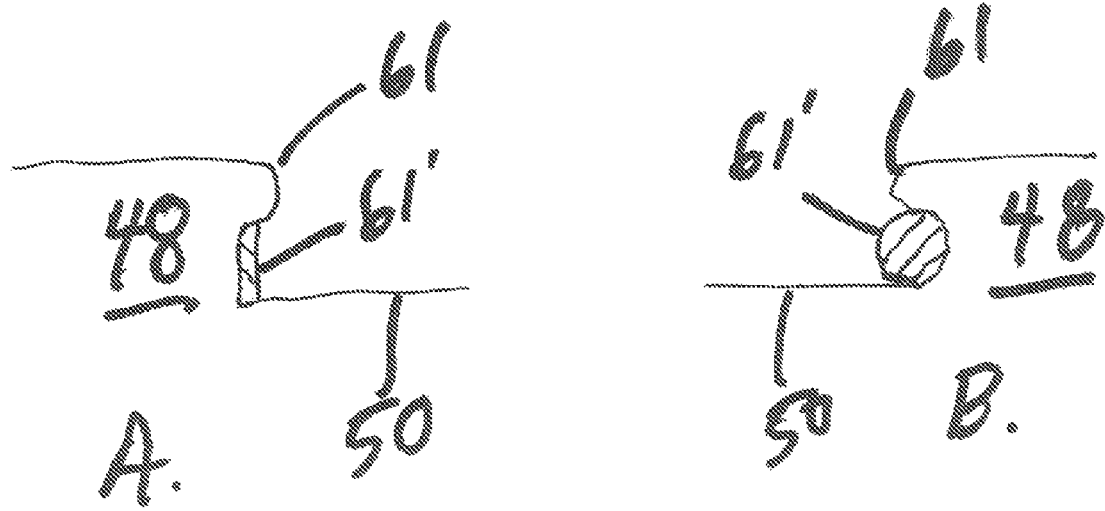
FIGS. 5A-5B are elevational side views in cross section of related embodiments of the invention wherein the interference structures comprise complementary structures a first structure formed in the inner periphery of a recess formed in the shroud member and a removable second structure residing in abutting relation to the first structure.

FIGS. 5A-5B are enlarged elevational side views in cross section of related embodiments of the invention wherein the interference structures comprise complementary structures a first structure 61 formed in the inner periphery of a recess formed in the shroud member 48 and a removable second structure 61' residing in abutting relation to the first structure 61. Although depicted in FIGS. 5A-5B the major surface of the recessed area 50 can comprise an open aperture 50. The second structure 61' can comprise any biocompatible resilient material such a resin-based polymer or the like. Optionally, the second structure 61' can be adhered to the shroud 48 and/or a portion of the first structure 61. The second structure 61' functions as a gasket or seal between the abutting portions of shroud 48 and electrode 54. While not depicted herein, the second structure 61' can be configured as a single C-shaped member that receives the periphery of either the recess (or aperture) 50 or the shroud member 48. Alternatively, the second structure can be configured with opposing C-shaped geometry adapted to receive both either the recess (or aperture) 50 and the shroud member 48.

Figure 6:
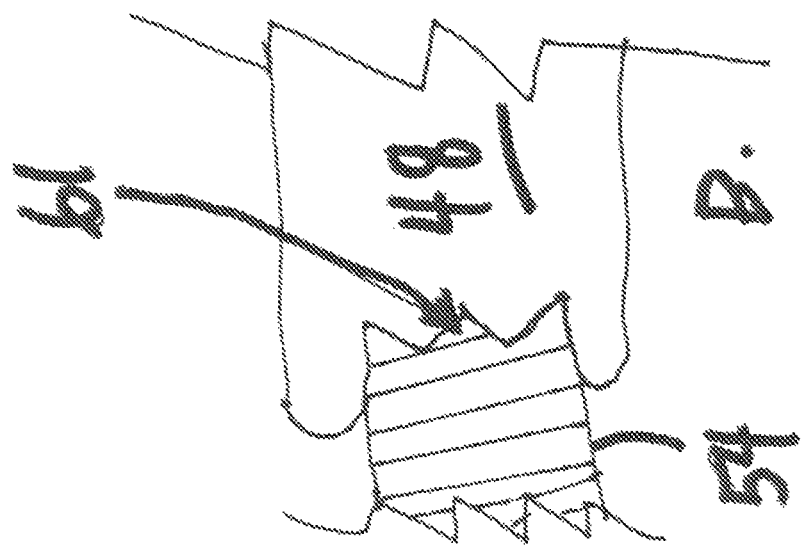
FIGS. 6A-6B are elevational views in cross section of related embodiments of the invention wherein cooperatively configured edge portions of the aperture in the shroud and the electrode provide a gap-free interface between the electrode and the shroud while also retaining the assembly in place.
Figure 6:
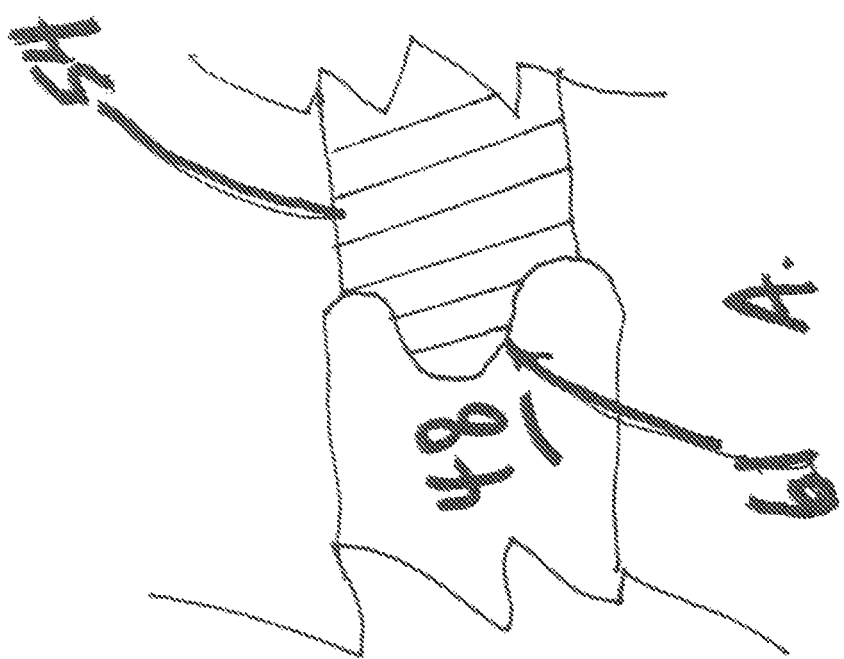

FIGS. 6A-6B are enlarged elevational views in cross section of related embodiments of the invention wherein cooperatively configured edge portions of the aperture 50 in the shroud 48 and the electrode 54 provide a gap-free interface (denoted by arrow 61) between the electrode 54 and the shroud 48 while also retaining the assembly parts firmly in place. The gap-free interface 61 can optionally include a second structure (e.g., the structure 61' of FIGS. 5A-5B) and/or medical grade adhesive between the shroud 48 and the recess or aperture 50. Such a second structure 61' can have curvilinear, regular, or irregular surface features that corresponds to the abutting structure (i.e., edges of recess or aperture 50 and electrode 54).

The edge features of shroud and/or the electrode can be fabricated using a variety of techniques such as molding, milling, computer numerically controlled (CNC) machinery, and the like.

Accordingly, a number of embodiments and aspects of the invention have been described and depicted although the inventors consider the foregoing as illustrative and not limiting as to the full reach of the invention. That is, the inventors hereby claim all the expressly disclosed and described aspects of the invention as well as those slight variations and insubstantial changes as will occur to those of skill in the art to which the invention is directed. The following claims define the core of the invention and the inventors consider said claims and all equivalents of said claims and limitations thereof to reside squarely within their invention.

The invention claimed is:

1. A subcutaneous cardiac activity sensing shroud, comprising:
   a shroud member for location adjacent at least a part of the peripheral portion of a housing for an implantable medical device (IMD), said shroud member including one of a recessed region and an aperture; and
   a substantially planar, plate-type electrode having a periphery that mechanically sealingly interlocks to one of the recessed region and the aperture,
   wherein at least a portion of an interior periphery of said recessed region or said aperture includes an interference structure configured to sealingly receive the electrode when said electrode is disposed therein.

2. A shroud according to claim 1, wherein said interference structure comprises a resilient material.

3. A shroud according to claim 1, further comprising a compressible member disposed intermediate the electrode and the shroud where the electrode and the shroud are abutting each other.

4. A shroud according to claim 3, wherein the compressible member comprises a resin-based member.

5. A shroud according to claim 3, wherein the compressible member comprises a biocompatible gasket and further comprising a medical grade adhesive coupled between one of: the biocompatible gasket and the electrode and the biocompatible gasket and the shroud.

6. A shroud according to claim 3, wherein the compressible member comprises a member having a C-shaped cross-sectional configuration.

7. A shroud according to claim 3, wherein the compressible member comprises a member having opposing C-shaped cross sectional configuration.

8. A shroud according to claim 1, further comprising an elongated conductor coupled to one of a major surface of the electrode and a peripheral portion of the major electrode.

9. A shroud according to claim 8, wherein the elongated conductor comprises an integrally formed structure with the electrode.

10. A shroud according to claim 1, wherein the electrode comprises one of a titanium material and a platinum material.

11. A shroud according to claim 1, further comprising medical grade adhesive disposed around between at least a part of the periphery of the electrode and the periphery of the recessed region or the aperture.

12. A shroud according to claim 1, wherein the electrode further includes a coating on at least a major surface thereof.

13. A shroud according to claim 12, wherein the coating comprises one of a nitride coating, a carbon black coating, a time-release coating.

14. A subcutaneous cardiac activity sensing shroud, comprising:
   a shroud member for location adjacent at least a part of the peripheral portion of a housing for an implantable medical device (IMD), said shroud member including one of a recessed region and an aperture;
   a substantially planar, plate-type electrode having a periphery that mechanically sealingly interlocks to one of the recessed region and the aperture,
   wherein at least a portion of an interior periphery of said recessed region or said aperture includes an interference structure configured to sealingly receive the electrode when said electrode is disposed therein;
   an electrode aperture formed in a major surface of the electrode; and
   an additional interference structure, wherein the additional interference structure extends from a major surface of the recessed region and sealingly engages the electrode aperture.

15. A shroud according to claim 14, wherein the additional interference structure includes a continuous interference structure around the periphery thereof configured to sealingly engage the electrode aperture.

16. A method of fabricating a cardiac sensing shroud assembly, comprising:
   providing a resilient shroud member adapted to be mounted around at least a part of the peripheral portion of a housing for an implantable medical device (IMD);

forming one of a recessed region and an aperture in a peripheral portion of the shroud member; and compressing a substantially planar, plate-type electrode into positive engagement with an interference structure, wherein the interference structure promotes a mutually interlocking sealing relationship between the electrode and one of the recessed region and the aperture.

17. A method according to claim 16, wherein the interference structure comprises a gasket having a C-shaped cross section.

18. A method according to claim 16, further comprising:

coupling the shroud member around at least a part of the peripheral portion of the IMD, and wherein the IMD comprises one of: an implantable cardiac pacemaker, an implantable cardioverter-defibrillator, an implantable fluid delivery device, an implantable neurostimulator, an implantable gastric simulator.

\* \* \* \* \*